(12) United States Patent
Kitagawa

(10) Patent No.: US 6,827,904 B2
(45) Date of Patent: Dec. 7, 2004

(54) LIQUID DISPENSING APPARATUS AND AN AUTOMATIC ANALYZING APPARATUS USING THE SAME

(75) Inventor: Nobuhiro Kitagawa, Akashi (JP)

(73) Assignee: Sysmex Corporation, Hyogo (JP)

( * ) Notice: Subject to any disclaimer, the term of this patent is extended or adjusted under 35 U.S.C. 154(b) by 441 days.

(21) Appl. No.: 09/820,684

(22) Filed: Mar. 30, 2001

(65) Prior Publication Data

US 2001/0028863 A1 Oct. 11, 2001

(30) Foreign Application Priority Data

Mar. 31, 2000 (JP) .......................................... 2000-099774
Mar. 21, 2001 (JP) .......................................... 2001-079955

(51) Int. Cl.⁷ .............................. B01L 3/02; B01L 3/00; G01N 21/00; B65D 55/02; B65D 41/02
(52) U.S. Cl. .......................... 422/100; 422/99; 422/63; 422/102; 422/65; 222/556; 215/211; 215/235; 215/239; 220/260; 220/263
(58) Field of Search ................................. 215/211, 235, 215/239; 220/260, 263, 549; 422/102, 99, 100, 63–65; 222/556

(56) References Cited

U.S. PATENT DOCUMENTS

| 4,198,483 A | * | 4/1980 | Sogi et al. ................ 435/309.1 |
| 4,498,149 A | * | 2/1985 | Yoshida .......................... 704/3 |
| 4,578,244 A | * | 3/1986 | Cosgrove et al. .............. 422/65 |
| 5,628,962 A | * | 5/1997 | Kanbara et al. ............... 422/63 |
| 5,674,741 A | * | 10/1997 | Watanabe et al. ......... 435/283.1 |
| 5,948,360 A | * | 9/1999 | Rao et al. ....................... 422/65 |
| 6,060,022 A | * | 5/2000 | Pang et al. .................... 422/65 |
| 6,426,225 B1 | * | 7/2002 | Lewis et al. .................... 436/8 |
| 6,436,349 B1 | * | 8/2002 | Carey et al. ................... 422/64 |
| 6,444,170 B1 | * | 9/2002 | Heid et al. ..................... 422/65 |
| 6,458,324 B1 | * | 10/2002 | Schinzel ....................... 422/65 |
| 6,503,455 B1 | * | 1/2003 | Kidd .......................... 422/102 |
| 2002/0041828 A1 | * | 4/2002 | Spitz et al. .................... 422/64 |

FOREIGN PATENT DOCUMENTS

| JP | 57-185964 | 11/1982 |
| JP | 64-061667 A | 3/1989 |
| JP | 8-094624 A | 4/1996 |
| JP | 8-160050 A | 6/1996 |
| JP | 10-311835 A | 11/1998 |

* cited by examiner

Primary Examiner—Jill Warden
Assistant Examiner—Brian R. Gordon
(74) Attorney, Agent, or Firm—Birch, Stewart, Kolasch & Birch, LLP (57) ABSTRACT

A liquid dispensing apparatus, includes a container for containing a liquid, a container setting part for setting the container, a dispensing mechanism part having a pipette for drawing and dispensing the liquid, a raising/lowering part for raising and lowering the pipette, a base for holding the raising/lowering part and provided with a projecting part, and a base driving part for moving the base. A lid capable of being opened/closed with an opening/closing pivot part is coupled to the container, and the lid is provided with a hook part projecting upward from the lid for engaging with the projecting part, which opens the lid by abutting against the hook part and moving the hook part toward the pivot part side of the container as the base moves relatively to the container and retains the state of the lid opened.

11 Claims, 10 Drawing Sheets

LIQUID DISPENSING APPARATUS AND AN AUTOMATIC ANALYZING APPARATUS USING THE SAME

BACKGROUND OF THE INVENTION

1. Field of the Invention

The present invention relates to a liquid dispensing apparatus for automatically opening a lid of a container to draw liquid from within a container and then dispense the liquid, and more particularly to an automatic analyzing apparatus provided with such a liquid dispensing apparatus.

2. Description of the Related Art

It is generally performed to prepare and analyze a sample by dispensing specimens such as blood serum and blood plasma and test reagents such as reaction agents and diluents, which are contained in containers, with a liquid dispensing apparatus such as a dispensing pipette after drawing from them. Particularly, in tests such as a blood coagulation test and an immunoassay, there are used automatic analyzers dispensing a plurality of specimens and test reagents successively and analyzing the reaction thereof. These automatic analyzers are different in the timing of replacement of their reagents since the amount of reagents consumed and the number of tests requested vary greatly in each analyzing item. Further, some analyzers require much time from the start to the end of analyses due to setting many specimen containers and analyzing many items. Therefore, the analyzer may be used in a state in which test reagent containers and specimen containers are left set at these analyzers for a long period of time.

Thus, when reagent containers and specimen containers are left set at these analyzers for a long period of time, evaporation/drying and mixing of dust cause deterioration of reagents or contamination of specimens and adversely affect the results of the analysis. So, to enhance the stability in storage, an opening of a container has been reduced in size or a container holding part has been kept cool. However, it is difficult to prevent the deterioration of reagents and specimens by only these means.

Consequently, there are presented an apparatus provided with a mechanism for automatically closing an opening of a reagent container with a lid except when drawing a reagent to prevent the deterioration of the reagent.

(a) Automatic analyzers which are provided with a mechanism section including a member corresponding to an opening of a reagent container and has a function of blocking an opening of a reagent container by operating the mechanism section automatically are disclosed in Japanese Unexamined Utility Model Publication No. Sho 57(1982)-185964, Japanese Unexamined Patent Publication No. Hei 8(1996)-160050 and Japanese Unexamined Patent Publication No. Hei 10(1998)-311835.

(b) In Japanese Unexamined Patent Publication Nos. Sho 64(1989)-61667 and Hei 8(1996)-94624, there are disclosed automatic analyzers, which a container to which a lid is connected is used in as a reagent container and a rotation mechanism with a member catching the lid is provided at, having a function of pulling and opening the lid of the reagent container by rotating the rotation mechanism.

In the apparatus of a conventional type described in above group (a), the mechanism part for blocking the opening of the container has to be configured to correspond to the container and therefore the constitution of the apparatus subjects to constraints. And, when reagents adhere to the member blocking the opening, contamination of a reagent to be used next may arise. Further, since the container and the lid are separated, it is required to attach and detach the lid before and after measuring and to preserve the lid at another location during measuring, and therefore it requires manpower.

In the apparatus of a conventional type described in the above group (b), to solve this problem, a lid is coupled to a reagent container. However, the automatic analyzer requires the rotation mechanism and a driving mechanism for letting the rotation mechanism catch the lid of the reagent container. Therefore, the constitution and operational controls of these mechanisms becomes complicated, and incorporating such complex mechanisms particularly into the automatic analyzer causes upsizing of the apparatus and lowering of the speed of the treatment due to the complexity of operational controls. Furthermore, since the lid of the reagent container needs to be configured to retain a state of the lid of the reagent container opened after being opened by the rotation mechanism, the constitution is limited.

SUMMARY OF THE INVENTION

It is an object of the present invention to provide a liquid dispensing apparatus which allows a lid of a container to be opened and closed with a simple constitution and control. And it is also an object of the present invention to provide a liquid dispensing apparatus being capable of using a container having a high degree of flexibility in a structure with respect to a container to be used.

It is another and further object of the present invention to provide an automatic analyzing apparatus provided with such a liquid dispensing apparatus.

In accordance with the present invention, there is provided a liquid dispensing apparatus, including a container for containing a liquid; a container setting part for setting the container; and a dispensing mechanism part having a pipette for drawing and dispensing the liquid, a raising/lowering part for raising and lowering the pipette, a base for holding the raising/lowering part and a base driving part for moving the base, thereby enabling to act the pipette at a suitable position, wherein a lid being capable of being opened/closed with an opening/closing pivot part is coupled to the container, and the lid is provided with a hook part projecting upward for engaging, and the base is provided with a projection part for engaging, which opens the lid by abutting against the hook part and moving the hook part toward the pivot part side of the container as the base moves relatively to the container and retains the state of the lid opened.

In such a liquid dispensing apparatus, it becomes possible to open the lid and to retain the state of the lid opened during drawing/dispensing of the pipette through the relatively simple structural addition of providing the conventional lid with the hook part and the conventional base with the projection part.

Furthermore, an automatic analyzing apparatus of the invention may include the liquid dispensing apparatus described above.

DETAILED DESCRIPTION OF THE PRESENT INVENTION

A container used in the present invention for containing liquid is a specimen container and/or a reagent container. The container has an opening at an upper portion, and a lid capable of being opened/closed with an opening/closing pivot part is coupled to the container. The lid is configured so as to block the opening of the container. Preferably, the lid is configured so as to have a construction which may seal the container.

The container setting part in the present invention is a portion at which a rack for holding one or more specimen containers is placed, a portion to which specimen containers are transferred by a transfer apparatus, and a portion at which reagent containers are placed. A movable container setting part may also be used as required.

It is preferred that the pipette in the present invention has a pipette body and a liquid metering means provided to the pipette body, such as a syringe or a pump, and operates as follows in, for example, the automatic analyzing apparatus. That is, when the pipette body is inserted into the specimen container or the reagent container from which the liquid is drawn, the liquid metering means connected to the pipette body starts drawing liquid and takes a definite amount of the specimen or the reagent separately. When the pipette body is moved toward a reaction vessel to which the specimen or the reagent is to be discharged and inserted into the reaction vessel, the liquid metering means starts discharging and dispenses a predetermined amount of the specimen or the reagent.

Then, washing water or air is supplied into the pipette body and discharged from a tip of the pipette. Or, reversely, washing water is drawn from a tip of the pipette body and discharged therefrom.

The pipette body thus washed is relatively moved again among the specimen container, the reagent and container, and the reaction vessel.

It is preferred that the raising/lowering part in the present invention may move the pipette precisely in a vertical direction by a drive of a belt looped over pulleys or a ball screw. It is preferred that the base driving part in the present invention may move the base precisely in a horizontal direction by a drive of a belt looped over pulleys or a ball screw.

The hook part formed on the lid is a part projecting outward and upward from the lid. To retain the state of the lid opened, a part in a valley form, which is V-shaped or U-shaped as viewed from the pivot part side of the lid, is formed between the hook part and the lid. Therefore, preferably, the hook part is formed so as to project from a location on a side of the pivot part. A shape of the hook part is selected as appropriate so as to correspond to a shape of the projection part of the dispensing mechanism part.

Preferably, the container is configured in such a way that the direction of the opening/closing of the lid is consistent with a specified direction when the container is set at the container setting part. For instance, when the container body and the lid are formed integrally or when, even though not formed integrally, the container body to which the lid can be attached in only one direction is used, configurations of the container and the container setting part are selected as appropriate in such a way that the container may be set in only one definite direction relative to the container setting part. When the relative direction of the lid is not determined in attaching the lid to the container body, it is possible to match the direction of the opening/closing of the lid with the specified direction in setting containers, for instance, by adopting a structure enabling lids of a plurality of containers to be connected to each other. When containers configured like these are used, it is possible to simplify further the motion of the opening/closing of the container.

Figure 8:
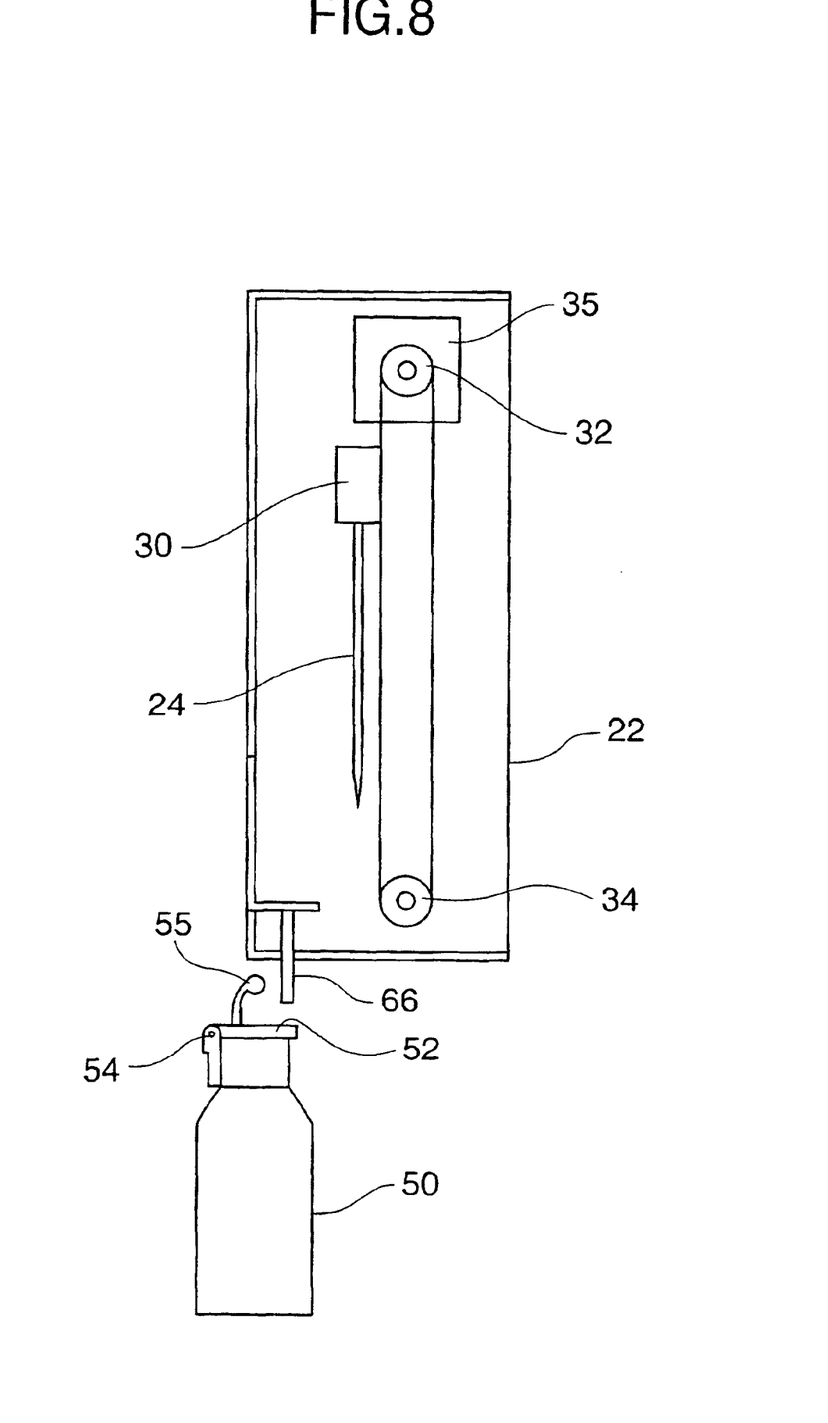
FIG. 8 is a view showing an another embodiment of a projection part.

The projection part provided at the base of the dispensing mechanism part in the present invention is a portion which may open the lid by making the hook part of the lid butt against the projection part from the reverse side of the pivot part of the lid with the relative movement of the base to the container and by pressing the hook part of the lid through moving the base toward the pivot part side of the lid and retain the state of the lid opened through entering between the lid and the hook part of the lid. When the shape of the projection part is selected so as to be adapted to the lid and the hook part of the lid, it is acceptable only to provide the base with a mere protrusion as illustrated in FIG. 8. Or, when the projection part is configured so as to retract and project only when required, a degree of flexibility in an arrangement and a constitution of the dispensing mechanism part and the reagent container are enhanced. For instance, it is possible to reciprocate a piston up and down as the projection part using an air cylinder or a solenoid.

EXAMPLE

Figure 1:
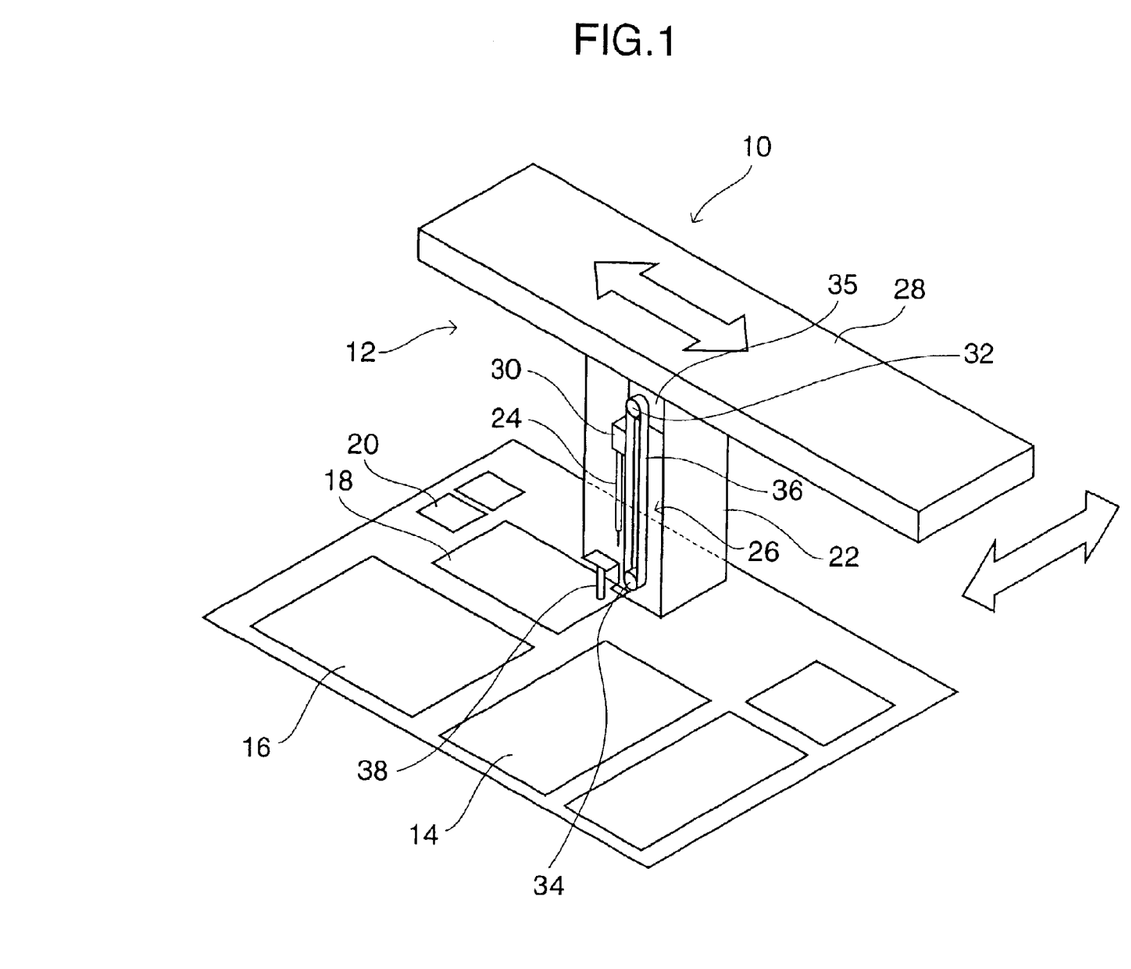
FIG. 1 is a perspective view showing an essential part of an automatic analyzing apparatus according to an embodiment of the present invention.

Hereinafter, by referring to the drawings, an embodiment of the present invention will be described. FIG. 1 is a perspective view showing an essential part of an automatic analyzing apparatus in accordance with the embodiment of the invention. A basic constitution of a reaction system and a measuring system are the same as a previously known apparatus.

An automatic analyzing apparatus 10 is mainly composed of a dispensing mechanism part 12, a specimen setting part 14, a reagent setting part 16, a reaction vessel setting part 18, and a measuring part 20. The dispensing mechanism part 12 is composed of a raising/lowering part 26 provided at a base 22 and raising/lowering a pipette 24 and a base driving part 28 moving the base 22 in two directions of X and Y axes.

The pipette 24 is held by a holder 30 at an upper end portion thereof and a top end of the pipette 24 is connected to a liquid metering part 31 (FIG. 2) through the medium of a tube. As the liquid metering part 31, here, a syringe driven by a motor is used. And, a washing liquid chamber for supplying washing liquid is connected to the syringe through the medium of a valve.

The raising/lowering part 26 includes a pair of pulleys 32, 34 provided in vertically-spaced relationship at a base 22, a motor 35 rotating/driving one of these pulleys 32, 34 and a belt 36 looped over these pulleys 32, 34 between them, and the holder 30 of the pipette 24 is secured to the belt 36 and thereby the raising/lowering part 26 is configured.

The projection part consists of a piston 38 of an air cylinder 40 (FIG. 7(*a*) etc.). The air cylinder 40 develops a state of projection of the piston 38 and a state of retraction thereof with working air supplied externally.

Figure 2:
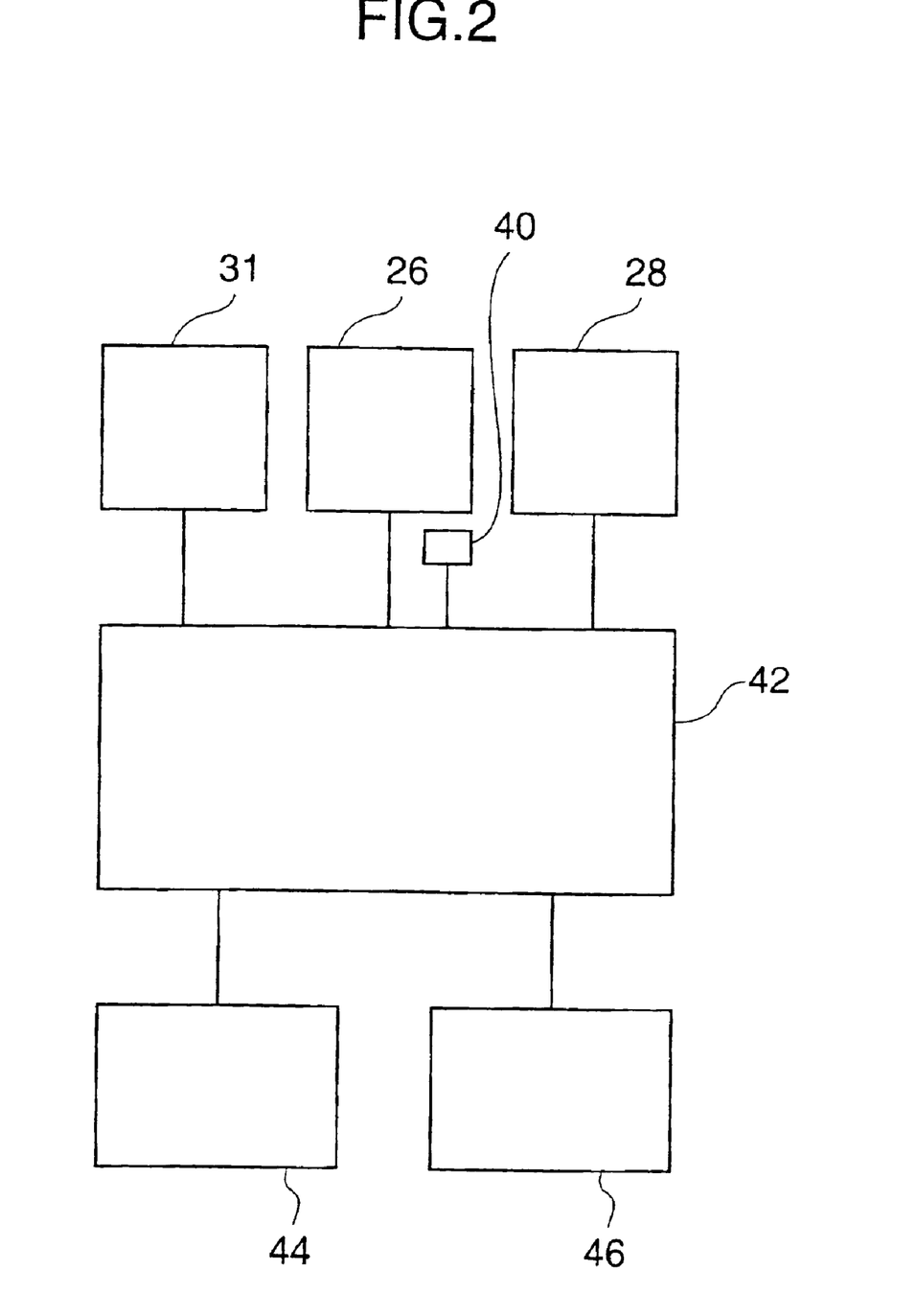
FIG. 2 is a block diagram showing the essential part of the automatic analyzing apparatus according to the embodiment of the present invention.

FIG. 2 is a block diagram of an essential part of the automatic analyzing apparatus 10. Reference numeral 42 indicates a control part including a microcomputer having a CPU, a ROM, a RAM, a timer and a counter and the like. The raising/lowering part 26 of the pipette 24, the liquid metering part 31, the base driving part 28, the air cylinder 40 being a driving source of the piston 38, and various kinds of positioning sensors are connected to the control part 42. Further a key-in-capable control panel 44 and an output part 46 displaying the measurements are connected the control part 42.

Figure 3:
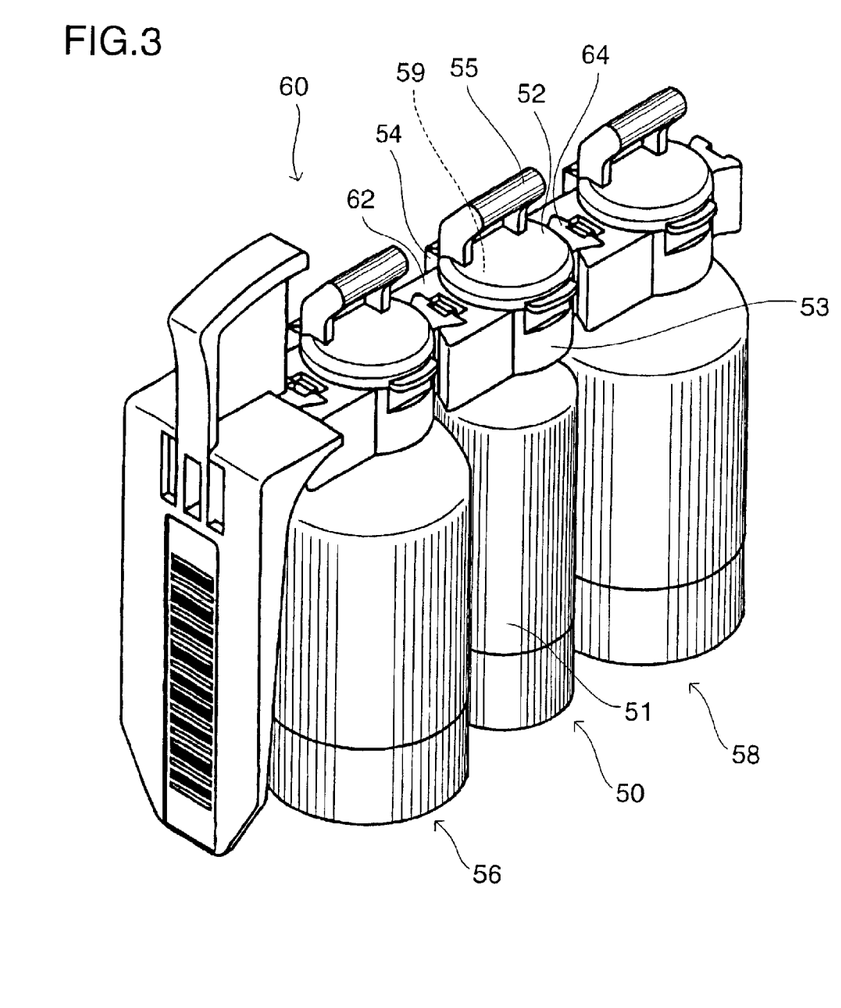
FIG. 3 is a perspective view of an example of the reagent unit used in the present invention.
Figure 4:
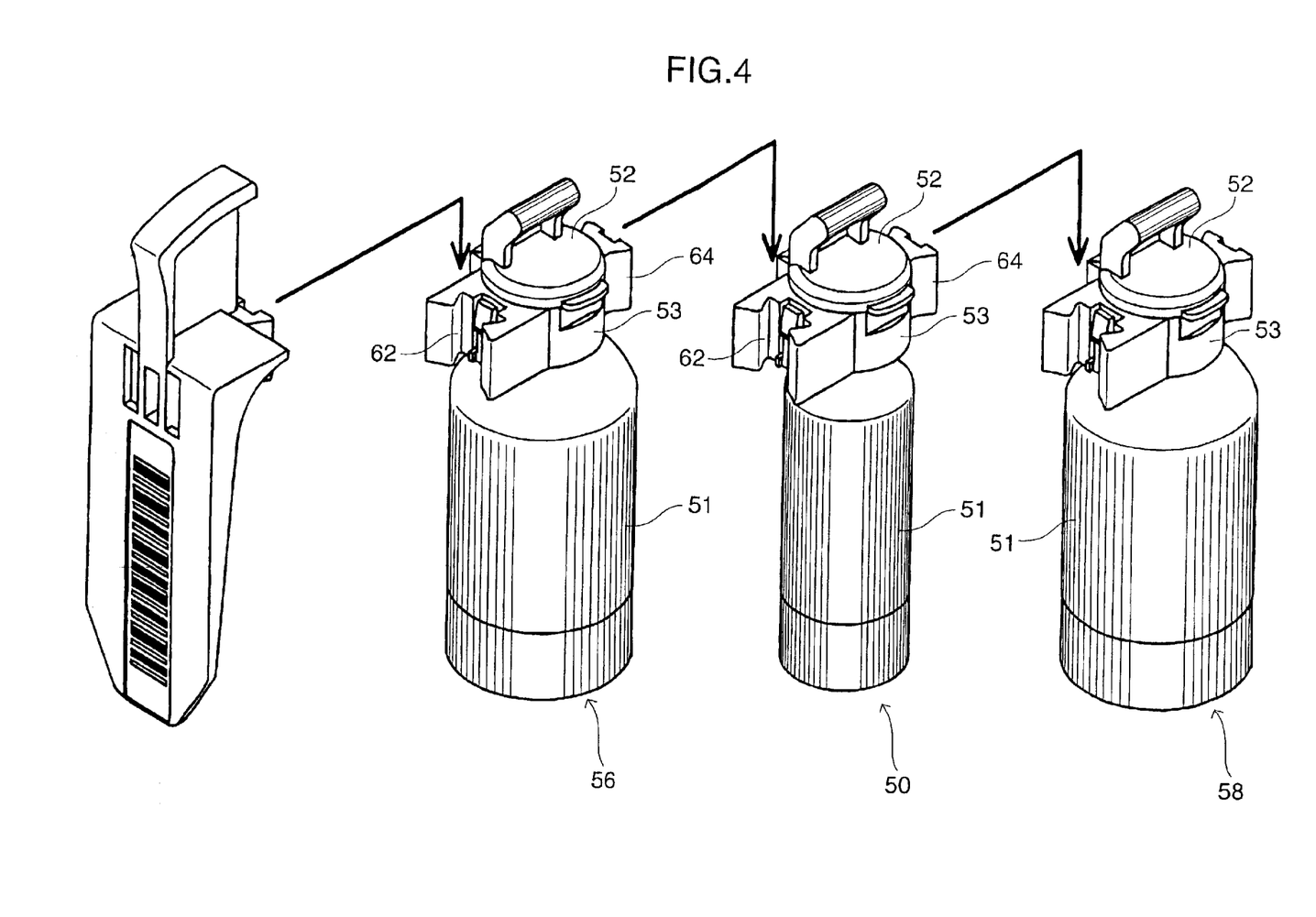
FIG. 4 is a perspective exploded view of the example of the reagent unit used in the present invention.

FIG. 3 and FIG. 4 are a perspective view and a perspective exploded view, respectively, of a reagent unit 60 used in the present invention, consisting of a plurality of reagent containers 50, 56, and 58. The lids 52 of reagent containers 50, 56, and 58 are adapted to be opened/closed, in which the lid 52 rotates about a pivot part 54 of a lid-support member 53 attached to a container body 51. A hook part 55 is provided on the top face of the lid 52.

Figure 5:
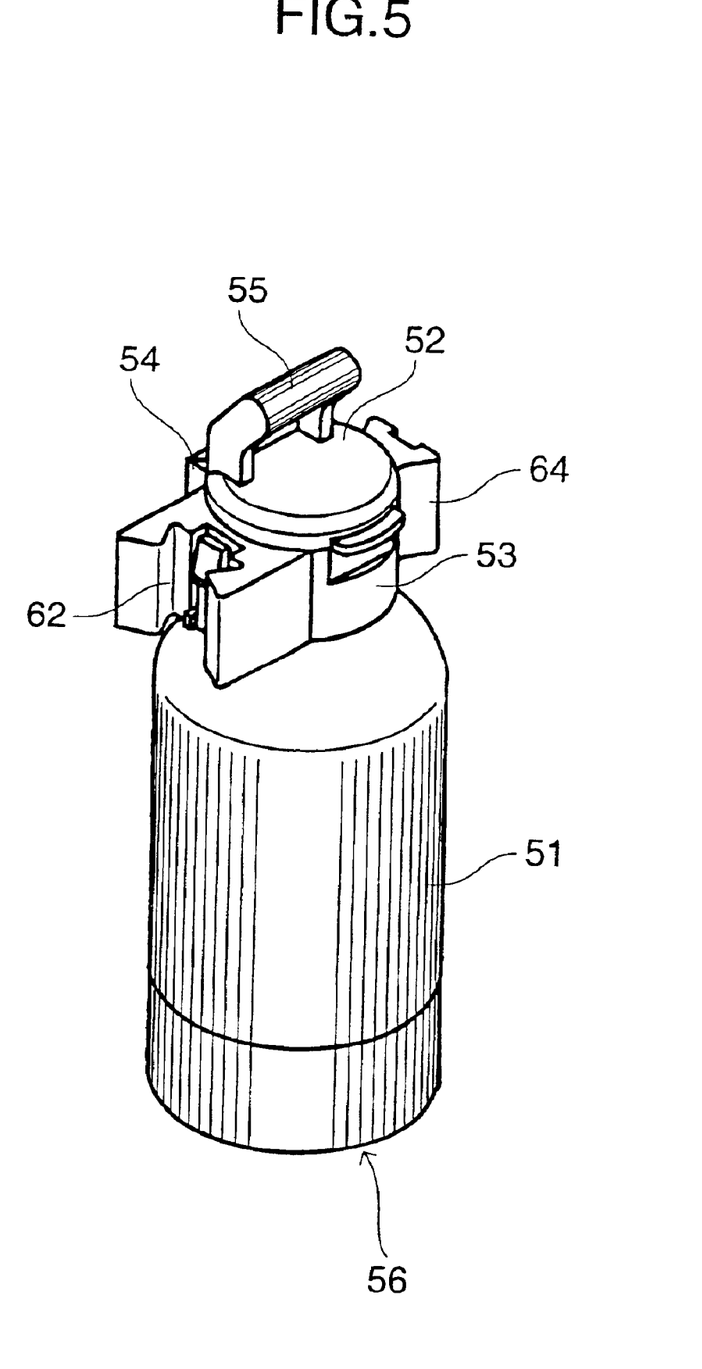
FIG. 5 is a perspective view of a container, of which a lid is closed, used in the present invention.
Figure 6:
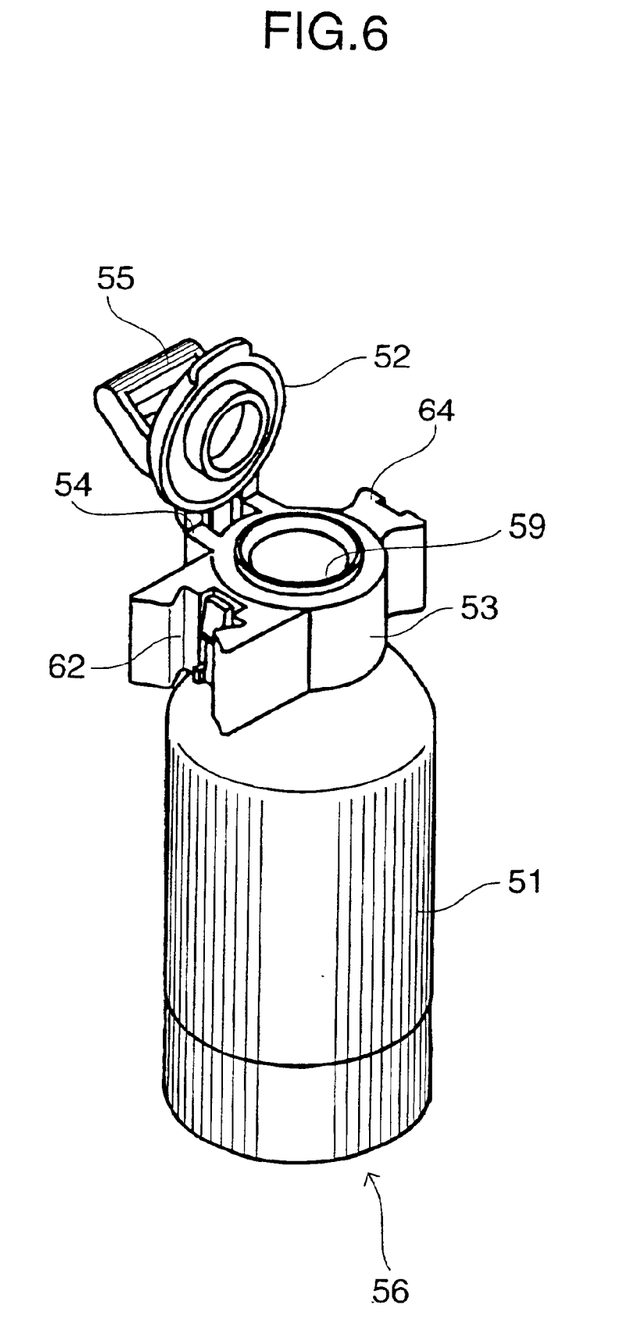
FIG. 6 is a perspective view of the container, of which the lid is opened, used in the present invention.

FIG. 5 and FIG. 6 are perspective views of one container 56 of which the lid is closed tightly and of which the lid is opened, respectively.

The lid-support member 53 of the reagent container 50 is provided with engaging parts 62, 64 so as to be coupled to lid-support members 53 of adjacent reagent containers 56, 58. By connecting more than one reagent containers 50, 56, 58 to each other to form the reagent unit 60 and holding the reagent unit 60 at the reagent setting part 16, the direction of the opening/closing of the lid 52 of respective containers is specified. Further, the lid 52 is configured to close tightly an opening 52 of the container body 51 by being pressed against the container body 51. Further, the reagent unit 60 is preserved in this condition in a refrigerator. When the reagent unit is set at the liquid dispensing apparatus, the state of being closed tightly is released manually, and openings 59 of container bodies are left closed under the lids 52 own weight.

Motion of the automatic analyzing apparatus 10 according to the present embodiment is described.

First, the base 22 is moved to the specimen setting part 14 by the base driving part 28, and the pipette 24 is lowered to draw the specimen in the specimen container by a specified amount. Then, the pipette 24 is raised, and the base 22 is moved laterally to a reaction vessel setting part 18, and the pipette 24 is lowered to dispense the drawn specimen.

Next, referring to FIGS. 7(*a*) to 7(*f*), motion of drawing in the reagent is described. FIG. 7 is a drawing illustrating the motion of the opening/closing of the lid.

Figure 7A:
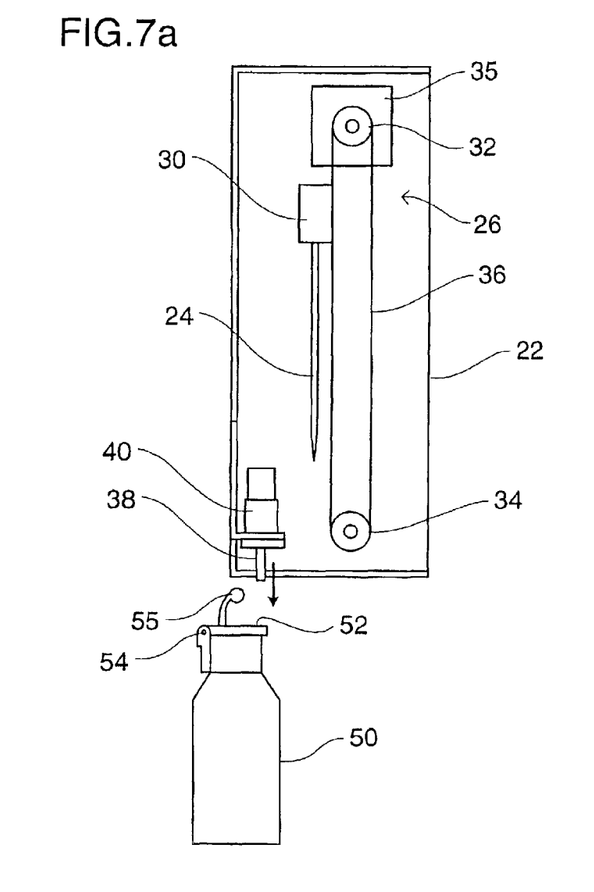
FIG. 7 is a view showing an opening/closing motion of the lid of the container in the embodiment of the present invention.

(a) The base 22 is moved laterally toward the reagent setting part 16 (movement towards the left direction in the drawing). The piston 38 of the air cylinder 40 is projected before the base 22 reaches the reagent setting part 16.

Figure 7B:
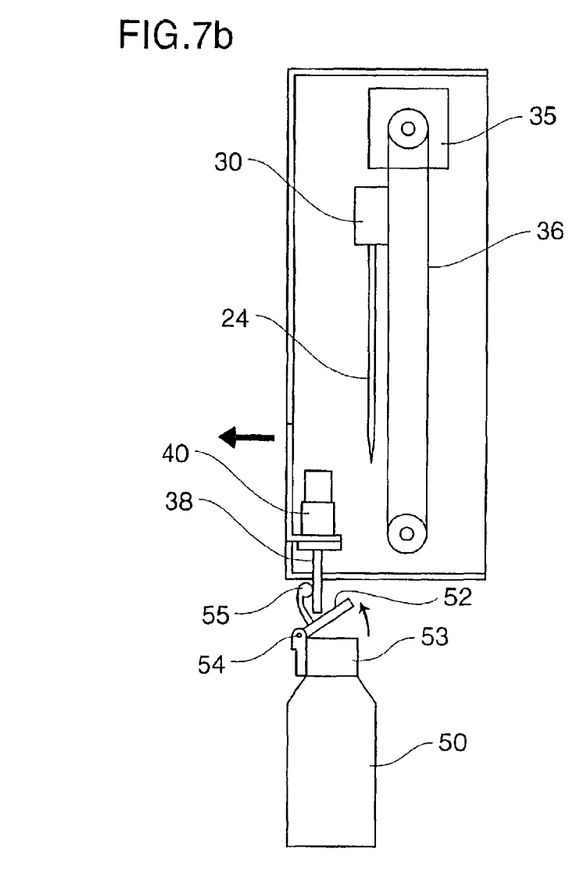

(b) As the base 22 is moved laterally in the left direction, the projection part 38 abuts against the hook part 55 of the reagent container 50 and moves the hook part 55 in the left direction, and thereby the projection part 38 rotates the lid 52 in counterclockwise direction about the pivot part 54 to open the lid 52.

Figure 7C:
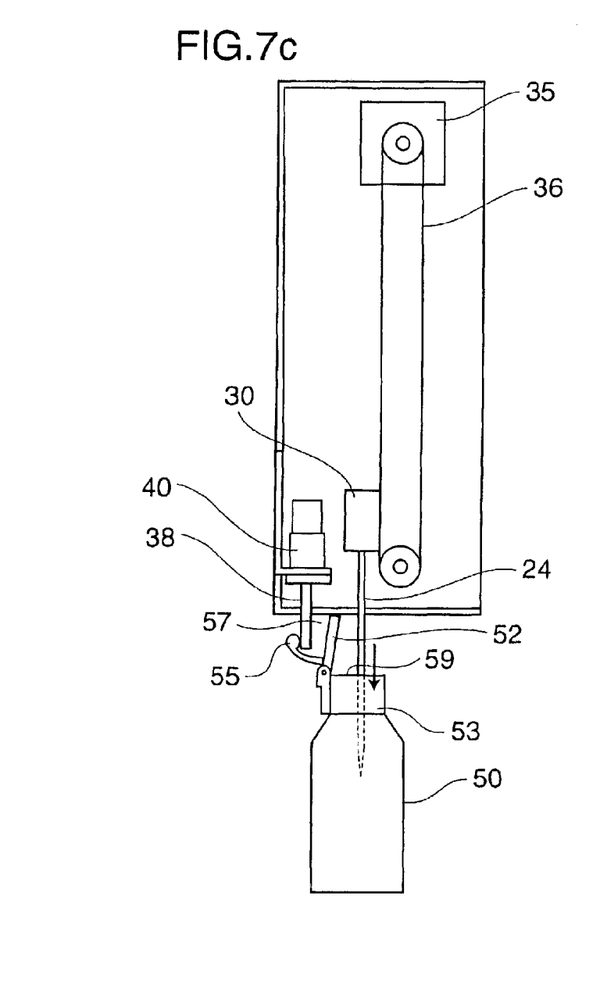

(c) When the base 22 stops, the pipette 24 is lowered to draw and takes a definite amount of reagent from the reagent container 50. In the meantime, since the projection part 38 positions in a V-shaped part in a valley form 57 formed by the hook part 55 and a top face of the lid 52, the lid 52 is retained in a state of the opening 59 of the container opened.

Figure 7D:
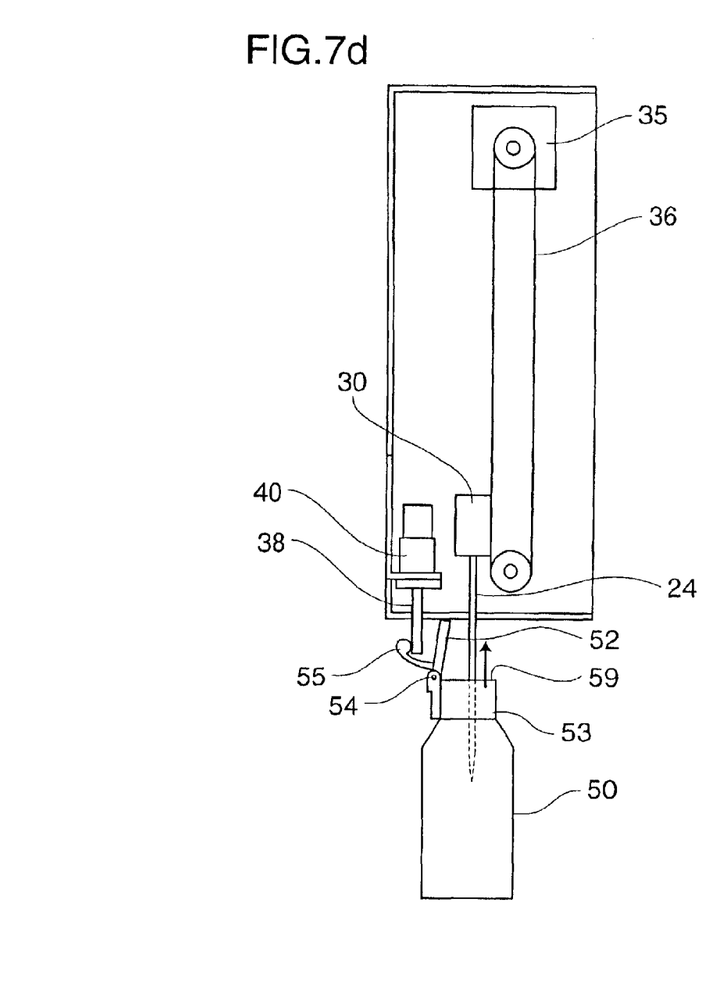

(d) After taking a definite amount of the reagent, the pipette 24 is raised.

Figure 7E:
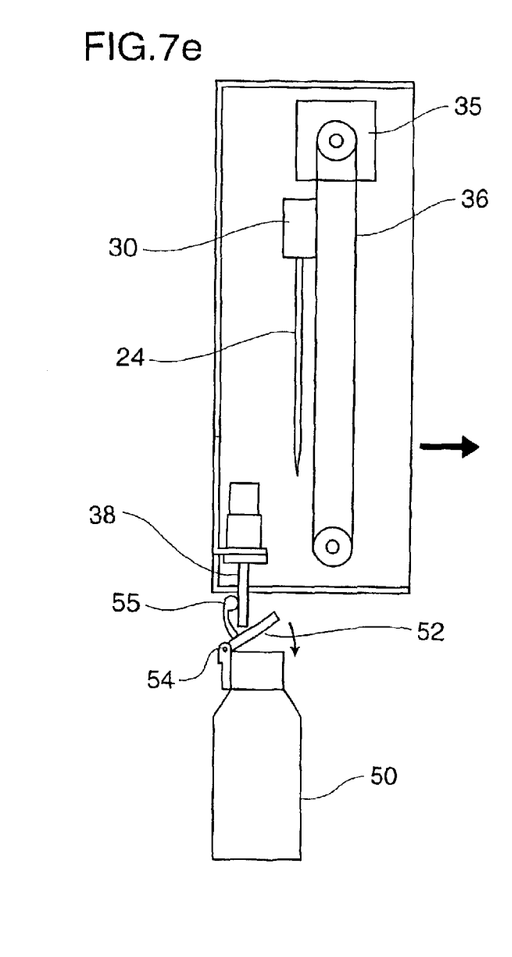

(e) As the base 22 is moved laterally to the right, the projection part 38 abuts against the top face of the lid 52 of the reagent container 50 and moves the top face to the right, and thereby the projection part 38 rotates the lid 52 in a clockwise direction about the pivot part 54 to close the lid 52.

Figure 7F:
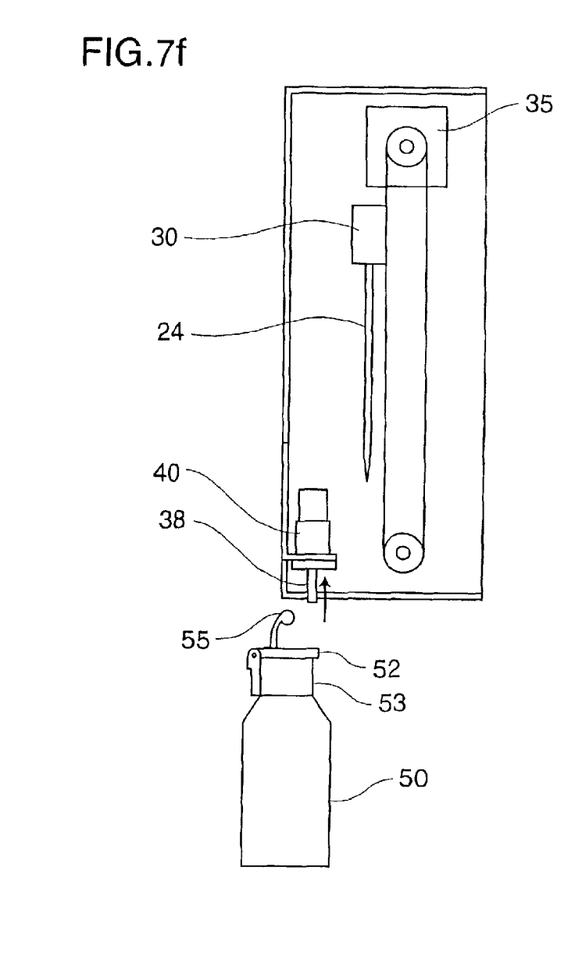

(f) Then, the piston 38 of the air cylinder 40 is retracted. The base 22 is moved to the reaction vessel setting part 18 and the drawn reagent in is dispensed into the specimen.

Up to this point, the example in which the projection part extends and retracts has been described but the projection part may be a rodlike member 66 which does not extend and retract as illustrated FIG. 8. Basic functions of the rodlike member 66 are the same.

The automatic analyzing apparatus used in the present invention is that in which a projection part is added to the base of the conventional dispensing mechanism part and a hook part is added to the lid of the conventional container and allows the lid to be opened and closed with a simple constitution. Since it is not particularly required to change the operations of dispensing, it is easy to control the operations and there is no possibility of lowering the speed of the treatment.

Further, since the lid of the reagent container is retained in a state of being opened, a problem of the closing of the lid during drawing with the pipette does not occur.

Furthermore, in the foregoing embodiment, the reagent container has a constitution in which the reagent container closes tightly by pressing the lid against the opening of the container. So, in FIG. 7(*e*), when the projection part 38 is controlled so as to press the lid downward after the lid 52 is rotated clockwise such that the lid 52 is closed by the movement of the projection part 38 accompanying the lateral movement of the base 22, it is possible to automatically close tightly the reagent container. It is possible to further prevent drying and deteriorating of the reagent by conducting such a control at the end of measuring operations. Further, the projection part 38 may also be configured in such a way that the lid 52 is released from the state of being closed tightly and rotated counterclockwise to be opened by the movement of the projection part 38 accompanying the lateral movement of the base 22 in restarting the measurement.

When the reagent container is automatically closed tightly by pressing the lid 52 downward with the projection part 38 in completing all measurement as described above, it is possible to preserve the reagent containers, which are taken out from the automatic analyzing apparatus, in a refrigerator as-is without the possibility of spilling the contents.

What is claimed is:

1. A liquid dispensing apparatus, comprising:
   a container for containing a liquid, said container having a lid coupled to the container adapted to open and close about an opening/closing pivot part and a hook part that projects upward from the lid when the lid is closed;
   a container setting part for setting said container; and
   a dispensing mechanism part having a pipette for drawing and dispensing the liquid, a raising/lowering part for raising and lowering the pipette, a base for holding the raising/lowering part and provided with a projection part adapted to engage with the hook part, and a base driving part for moving the base, thereby enabling the pipette and the projection part to move to a suitable operational position for dispensing or aspirating said liquid, wherein the base moves horizontally thereby the projection part opens the lid by abutting against the hook part and moving the hook part toward the pivot part side of the container and the pipette is lowered to a position for dispensing a liquid into or aspirating a liquid from said container.

2. The liquid dispensing apparatus as set forth in claim 1, wherein the pipette has a pipette body and a liquid metering means provided to the pipette body for metering liquid.

3. The liquid dispensing apparatus as set forth in claim 1, wherein the raising/lowering part includes a pair of pulleys provided in vertically-spaced relationship at the base, a motor rotating/driving one of these pulleys, and a belt looped over these pulleys.

4. The liquid dispensing apparatus as set forth in claim 1, wherein the container for containing the liquid is at least one of a specimen container and a reagent container, and the container setting part is any one among a portion at which a rack for holding a plurality of specimen containers is placed, a portion to which the specimen container is transferred by a transfer apparatus, and a portion at which a plurality of reagent containers are placed.

5. The liquid dispensing apparatus as set forth in claim 1, wherein the hook part projects upward from near the center of the lid and has an engaging portion approximately parallel to the pivot part.

6. The liquid dispensing apparatus as set forth in claim 1, wherein the projection part is adapted to extend such that the projection part engages with the hook part, and retract such that the projection part disengages from the hook part.

7. The liquid dispensing apparatus as set forth in claim 6, wherein the projection part is a piston of an air cylinder attached to the base and actuated with working air supplied externally.

8. The liquid dispensing apparatus as set forth in claim 1, wherein the projection part is a protrusion attached to the base.

9. The liquid dispensing apparatus as set forth in claim 1, wherein the container is configured in such a way that the direction of the opening/closing of the lid is consistent with a specified direction when the container is set at the container setting part.

10. The liquid dispensing apparatus as set forth in claim 1, wherein the projection part retains the state of the lid opened.

11. A liquid dispensing apparatus comprising:
a container for containing a liquid, said container having a lid;
a container setting part for setting said container; and
a dispensing mechanism part having a pipette for drawing and dispensing the liquid, a raising/lowering part for raising and lowering the pipette, a base for holding the raising/lowering part and provided with a projection part adapted to engage with the lid, and a base driving part for moving the base, thereby enabling the pipette and the projection part to move to a suitable operational position for dispensing or aspirating said liquid,
wherein the base moves horizontally thereby the projection part opens the lid by abutting against the lid and the pipette is lowered to a position for dispensing a liquid into or aspirating a liquid from said container.

* * * * *